United States Patent
An et al.

(10) Patent No.: US 10,071,116 B2
(45) Date of Patent: Sep. 11, 2018

(54) METHOD FOR MANUFACTURING HYDROGEN-SATURATED DEUTERIUM-DEPLETED WATER

(71) Applicant: H Bank Technology INC., New Taipei (TW)

(72) Inventors: I-Hsin An, New Taipei (TW); Chih-Kang Shih, New Taipei (TW)

(73) Assignee: H BANK TECHNOLOGY INC., New Taipei (TW)

(*) Notice: Subject to any disclaimer, the term of this patent is extended or adjusted under 35 U.S.C. 154(b) by 213 days.

(21) Appl. No.: 15/245,229

(22) Filed: Aug. 24, 2016

(65) Prior Publication Data

US 2017/0056440 A1    Mar. 2, 2017

(30) Foreign Application Priority Data

Aug. 28, 2015 (TW) .............................. 104128277 A

(51) Int. Cl.

| C02F 1/20 | (2006.01) |
|---|---|
| A61K 33/00 | (2006.01) |
| A23L 2/54 | (2006.01) |
| C02F 1/00 | (2006.01) |
| C02F 1/469 | (2006.01) |
| C02F 1/68 | (2006.01) |
| C02F 103/02 | (2006.01) |

(52) U.S. Cl.
CPC ................ *A61K 33/00* (2013.01); *A23L 2/54* (2013.01); *C02F 1/008* (2013.01); *C02F 1/4693* (2013.01); *C02F 1/68* (2013.01); *A23V 2002/00* (2013.01); *C02F 2103/026* (2013.01); *C02F 2201/46* (2013.01)

(58) Field of Classification Search
None
See application file for complete search history.

(56) References Cited

U.S. PATENT DOCUMENTS

| 2005/0109604 A1* | 5/2005 | Zlotopolski | ............ B01D 5/009 |
| | | | 203/10 |
| 2016/0249668 A1* | 9/2016 | Igarashi | ................... A23L 2/02 |
| | | | 426/72 |

FOREIGN PATENT DOCUMENTS

| JP | 3606466 B1 * | 1/2005 | ............... A23L 2/52 |
| JP | 2008006365 A * | 1/2008 | |
| JP | 2009011999 A * | 1/2009 | |
| JP | 2015208744 A * | 11/2015 | |

* cited by examiner

*Primary Examiner* — Melissa S Swain
(74) *Attorney, Agent, or Firm* — Bacon & Thomas, PLLC

(57) ABSTRACT

The present invention relatives to a method for manufacturing hydrogen-saturated deuterium-depleted water, comprising (a) providing a distilled or mineral water; (b) providing a hydrogen storage apparatus for providing a high purity hydrogen; (c) controlling a pressure of hydrogen gas between 3~8 bar at a working environment temperature of 10~28° C.; (d) controlling a flow velocity of hydrogen gas between 3~5 L/min and inletting hydrogen into the distilled or mineral water to produce a pressure difference to replace deuterium from the distilled water; and (e) controlling a working time between 30~90 mins to produce a hydrogen-saturated deuterium-depleted water. Therefore, a method for manufacturing hydrogen-saturated deuterium-depleted water with low consuming energy and low production cost is provided.

10 Claims, 2 Drawing Sheets

METHOD FOR MANUFACTURING HYDROGEN-SATURATED DEUTERIUM-DEPLETED WATER

CROSS REFERENCE TO RELATED APPLICATION

This application claims the benefits of the Taiwan Patent Application Serial Number 104128277, filed on Aug. 28, 2015, the subject matter of which is incorporated herein by reference.

BACKGROUND OF THE INVENTION

1. Field of the Invention

The present invention relates to a method for manufacturing hydrogen-saturated deuterium-depleted water, and more particularly to a method for manufacturing hydrogen-saturated deuterium-depleted water by means of inletting hydrogen gas into water to produce a pressure difference to replace deuterium from water.

2. Description of Related Art

The hydrogen-saturated water means the hydrogen gas dissolved in water in a saturated state. Ordinarily, a process of hydrogen-saturated water should be controlled by a way of a supercritical process to produce the hydrogen-saturated water. Besides, the hydrogen gas and water should be bound together to produce the hydrogen-saturated water; therefore, the hydrogen gas cannot still escape quickly even though the bottle cap is opened. Furthermore, the hydrogen-saturated water satisfied with the henry's law is the hydrogen water, of which the dissolved hydrogen content in water approaches the maximum dissolved hydrogen content, namely the dissolved hydrogen content is 2%.

The deuterium depleted water (DDW) is that the deuterium content of the water is reduced by a high-technology isotope separation to produce a high-end drinking water. The natural water on the earth's surface all includes deuterium, an isotope of hydrogen. Further, the water has normal deuterium contents suitable for dividing the tumor cells; therefore, many countries make efforts to research into reducing the deuterium contents of the water to produce the deuterium-depleted water. Furthermore, the deuterium-depleted water is widely used in many fields, such as cancer prevention, health care, beauty care and so on. Generally speaking, the deuterium content of tap water is more than 150 ppm, the deuterium content of groundwater of the desert is 180 ppm, the deuterium content of the glacier water is less than 150 ppm, and the deuterium content of the hydrogen-saturated deuterium-depleted water is less than 150 ppm. The studies show that a person drinks the water having few deuterium contents for a long period of time capable of inhibiting the growth of malignant cell, and prolong life; therefore, a growing number of people choice the hydrogen-saturated deuterium-depleted water to drink. However, the glacier water is present in the plateau far away from people; the costs of exploitation and transportation are huge. Hence, the glacier water is not exploited and used extensively. Besides, the hydrogen-saturated deuterium-depleted water produced through a traditional distillation method is very limited, because the difference of boiling point between hydrogen gas and deuterium gas are small and the dissipation energy between them is large.

Therefore, there is an urgent need for a method for manufacturing hydrogen-saturated deuterium-depleted water, which the hydrogen-saturated deuterium-depleted water is produced by inletting hydrogen gas into water to produce a pressure difference to replace deuterium from water and using preferred operating parameters, thereby enhancing dissolved hydrogen content in the water and reducing the deuterium content in the water to enhance the quality of the drinking water.

SUMMARY OF THE INVENTION

An object of the present invention is to provide a method for manufacturing hydrogen-saturated deuterium-depleted water, which the hydrogen-saturated deuterium-depleted water is produced by using the high purity hydrogen gas to replace deuterium gas and preferred operating parameters to provide high-quality drinking water. Therefore, the hydrogen-saturated deuterium-depleted water can prevent the growth of malignant tumor and prolong life.

To achieve the above object, the present invention provides a method for manufacturing hydrogen-saturated deuterium-depleted water, comprising (a) providing a distilled or mineral water; (b) providing a hydrogen storage apparatus for providing a high purity hydrogen gas; (c) controlling a pressure of hydrogen gas between 3~8 bar at a working environment temperature of 10~28° C.; (d) controlling a flow velocity of hydrogen gas between 3~5 L/min and inletting hydrogen into the distilled or mineral water to produce a pressure difference to replace deuterium from the distilled water; and (e) controlling a working time between 30~90 mins to produce a hydrogen-saturated deuterium-depleted water.

In above-mentioned method for manufacturing hydrogen-saturated deuterium-depleted water, the hydrogen storage apparatus may include a hydrogen storage alloy, and the hydrogen storage apparatus can store safely hydrogen atoms. Further, the high purity hydrogen gas in the gas form is supplied to the distilled or mineral water. In above-mentioned method for manufacturing hydrogen-saturated deuterium-depleted water, a purity of the high purity hydrogen gas can be in a range of 99.9999% or more to show most stable quality of hydrogen gas.

In above-mentioned method for manufacturing hydrogen-saturated deuterium-depleted water, the working environment temperature may be randomly varied based on the user's requirements or quality requirements of the hydrogen-saturated deuterium-depleted water; wherein in one aspect of the present invention, the working environment temperature can be between 20 to 28° C., and in the other aspect, the working environment temperature can be between 24 to 26° C., but the present invention is not limited thereto. In above-mentioned method for manufacturing hydrogen-saturated deuterium-depleted water, a pressure of the high purity hydrogen gas may be randomly varied based on the user's requirements or quality requirements of the hydrogen-saturated deuterium-depleted water; wherein in one aspect of the present invention, the pressure of hydrogen gas is between 6 to 8 bar, and in the other aspect, the pressure of hydrogen gas is between 5 to 7 bar, but the present invention is not limited thereto.

In above-mentioned method for manufacturing hydrogen-saturated deuterium-depleted water, a flow velocity of the high purity hydrogen gas may be randomly varied based on the user's requirements or quality requirements of the hydrogen-saturated deuterium-depleted water; wherein in one aspect of the present invention, the flow velocity of the high purity hydrogen gas is between 3 to 5 L/min, but the present invention is not limited thereto. In above-mentioned method for manufacturing hydrogen-saturated deuterium-depleted water, the working time may be randomly varied based on the user's requirements or quality requirements of the hydrogen-saturated deuterium-depleted water; wherein in one aspect of the present invention, the working time is between 70 to 90 minutes, and in the other aspect of the present invention, the working time is between is 50 to 70 minutes, but the present invention is not limited thereto. In above-mentioned method for manufacturing hydrogen-saturated deuterium-depleted water, the working environment temperature, the pressure of the high purity hydrogen gas, the flow velocity of the high purity hydrogen gas and the working time can be controlled simultaneously to achieve an optimizing benefit.

In the well-known technology, a method for manufacturing the deuterium-depleted water may include: (1) a distillation method: using repeatedly distillation because of boiling point of hydrogen gas and deuterium gas to be different to produce the deuterium-depleted water; (2) a electrolytic method: adding appropriate solutes by means of a electrolytic method to produce the deuterium-depleted water; and (3) a cold method: using repeatedly cold method to cause a concentration difference to produce the deuterium-depleted water. The method for manufacturing hydrogen-saturated deuterium-depleted water of the present invention is by means of a replacement method to produce the deuterium-depleted water, which hydrogen gas is inlet to produce a pressure difference to replace deuterium from the distilled water. In above-mentioned method for manufacturing hydrogen-saturated deuterium-depleted water, a deuterium content of the hydrogen-saturated deuterium-depleted water is between 100 to 130 ppm. In another aspect of the present invention, the deuterium content of the hydrogen-saturated deuterium-depleted water is between 70 to 100 ppm. In above-mentioned method for manufacturing hydrogen-saturated deuterium-depleted water, the hydrogen-saturated water is produced and removed deuterium gas from distilled or mineral water to produce hydrogen-saturated deuterium-depleted water.

In the well-known technology, the method for manufacturing hydrogen water may include an additive method and an including method, which the additive method means purity hydrogen gas inletting into water, and the including method means high active material, such as magnesium, reacts with water to produce hydrogen gas which is included in raw water. The hydrogen-saturated water of the present invention means that the hydrogen water has dissolved hydrogen content in water approaching the maximum dissolved hydrogen content, and the saturation of the hydrogen water reaches upper limit. According to henry's law, a molarity of hydrogen gas dissolved in distilled or mineral water is directly proportional to a partial pressure of hydrogen gas while the distilled water achieved equilibrium in an enclosed container at normal temperature. In above-mentioned method for manufacturing hydrogen-saturated deuterium-depleted water, a solubility of hydrogen in the hydrogen-saturated deuterium-depleted water may be 1.5 to 2%.

In above-mentioned method for manufacturing hydrogen-saturated deuterium-depleted water, the hydrogen storage apparatus may comprise a pressure regulator valve for controlling a pressure of the purity hydrogen inletting into the distilled or mineral water, and a flow controller for controlling a flow velocity of hydrogen inletting into the distilled or mineral water. Besides, in above-mentioned method for manufacturing hydrogen-saturated deuterium-depleted water, the temperature of working environment is controlled by an air conditioner.

In above-mentioned method for manufacturing hydrogen-saturated deuterium-depleted water, the present invention further comprises a step (f) after step (d): standing and sealing the hydrogen-saturated deuterium-depleted water for 60 to 90 minutes. Further, the time of standing and sealing the hydrogen-saturated deuterium-depleted water may be randomly varied based on the user's requirements or quality requirements of the hydrogen-saturated deuterium-depleted water; wherein in one aspect of the present invention, the time of standing and sealing the hydrogen-saturated deuterium-depleted water is 70 to 80 minutes. In the manufacturing process, bonding of hydrogen gas and water is unstable because of turbulence; therefore, the hydrogen-saturated deuterium-depleted water needs to stand for 70 to 80 minutes to achieve a liquid-vapor equilibrium state.

In above-mentioned method for manufacturing hydrogen-saturated deuterium-depleted water, the present invention further comprises a step (g) after step (f): sterilized cold filling the hydrogen-saturated deuterium-depleted water to an encapsulating container by a sterilized box at room temperature; wherein the encapsulating container may be randomly varied based on the user's requirements or quality requirements of the hydrogen-saturated deuterium-depleted water. In one aspect of the present invention, the encapsulating container may be a glass material; and in another aspect of the present invention, the encapsulating container may be a stainless steel material, but the present invention is not limited thereto. Further, the encapsulating container of the present invention does not have a capillary phenomenon; therefore, the encapsulating container may achieve a totally-enclosed state. In above-mentioned method for manufacturing hydrogen-saturated deuterium-depleted water, an ultra-violet lamp, an ozone generator, a laminar flow hood or an alcohol burner are used in previous sealing process, middle sealing process or posterior sealing process at room temperature to achieve an asepsis state.

In above-mentioned method for manufacturing hydrogen-saturated deuterium-depleted water, the present invention further comprises a step (h) after step (g): liquid-vapor equilibrating the hydrogen-saturated deuterium-depleted water between 15 to 30 days to maintain a high concentration saturated state of the hydrogen-saturated deuterium-depleted water.

In summary, according to method for manufacturing hydrogen-saturated deuterium-depleted water, the working environment temperature, the pressure of the high purity hydrogen gas, the flow velocity of the high purity hydrogen gas and the working time can be controlled simultaneously to achieve an optimizing benefit. Besides, the method for manufacturing hydrogen-saturated deuterium-depleted water of the present invention is inlet hydrogen gas to replace deuterium gas, and maintains a high concentration saturated state of hydrogen-saturated deuterium-depleted water simultaneously.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENT

Hereinafter, the actions and the effects of the present invention will be explained in more detail via specific examples of the invention. However, these examples are merely illustrative of the present invention and the scope of the invention should not be construed to be defined thereby.

Example 1

Figure 1:
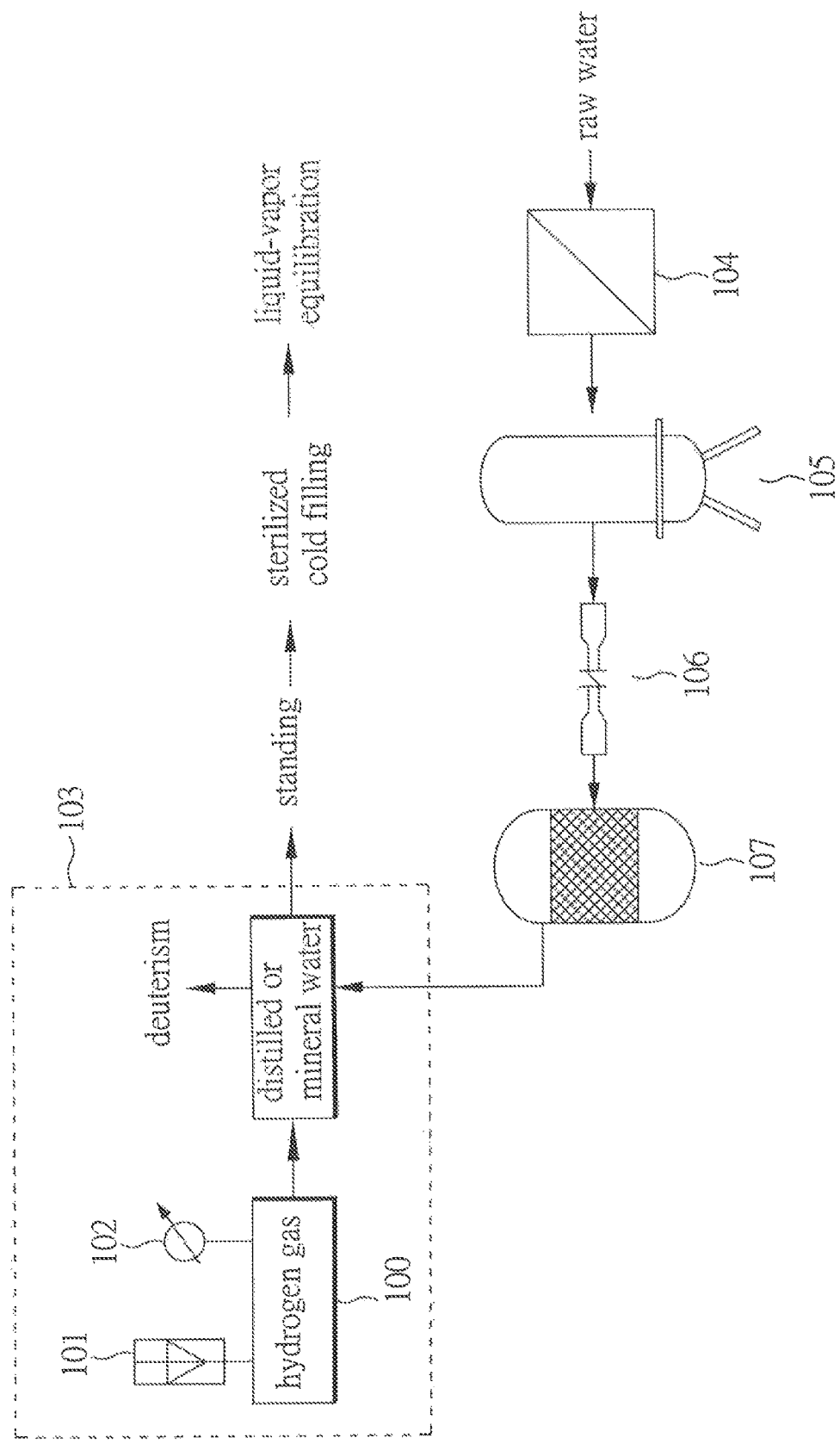
FIG. 1 shows a flow chart of the method for manufacturing hydrogen-saturated deuterium-depleted water according to Example 1 of the present invention.

In method for manufacturing hydrogen-saturated deuterium-depleted water of the present invention, a hydrogen gas is inlet into water to replace a deuterium gas, and maintains a high concentration saturated state of hydrogen-saturated deuterium-depleted water simultaneously. Please refer to FIG. 1, FIG. 1 shows a flow chart of the method for manufacturing hydrogen-saturated deuterium-depleted water according to Example 1 of the present invention. As shown in FIG. 1, first, a distilled or mineral water is provided, wherein the distilled water is produced by the raw water through an electric dialyzator 104, an ion exchanger 105, a counter-osmosis device 106, a distillation equipment 107 and the other appropriate processing method. Further, a hydrogen storage apparatus 100 is provided, and a high purity hydrogen gas is provided by the hydrogen storage apparatus 100. Secondly, the working environment temperature is controlled between 10 to 28° C. by a an air conditioner 103, and the pressure of the high purity hydrogen gas is controlled in a range between 3 to 8 bar by a pressure regulator valve 102. Furthermore, a flow velocity of high purity of hydrogen gas is controlled in a range of 3 to 5 L/min by a flow controller 101. Further, the high purity hydrogen gas is inlet into the distilled or mineral water to produce a pressure difference to replace deuterium gas from the distilled or mineral water, and working time is controlled for 60 minutes to form the hydrogen-saturated deuterium-depleted water. Moreover, the produced hydrogen-saturated deuterium-depleted water is stood and sealed for 60 minutes, and the hydrogen-saturated deuterium-depleted water is sterilized cold filled to an encapsulating container made of a glass material by a sterilized box at room temperature; wherein the encapsulating container does not have a capillary phenomenon to achieve a totally-enclosed state. Finally, the hydrogen-saturated deuterium-depleted water achieves a liquid-vapor equilibrium state to maintain a high concentration saturated state of the hydrogen-saturated deuterium-depleted water.

Figure 2:
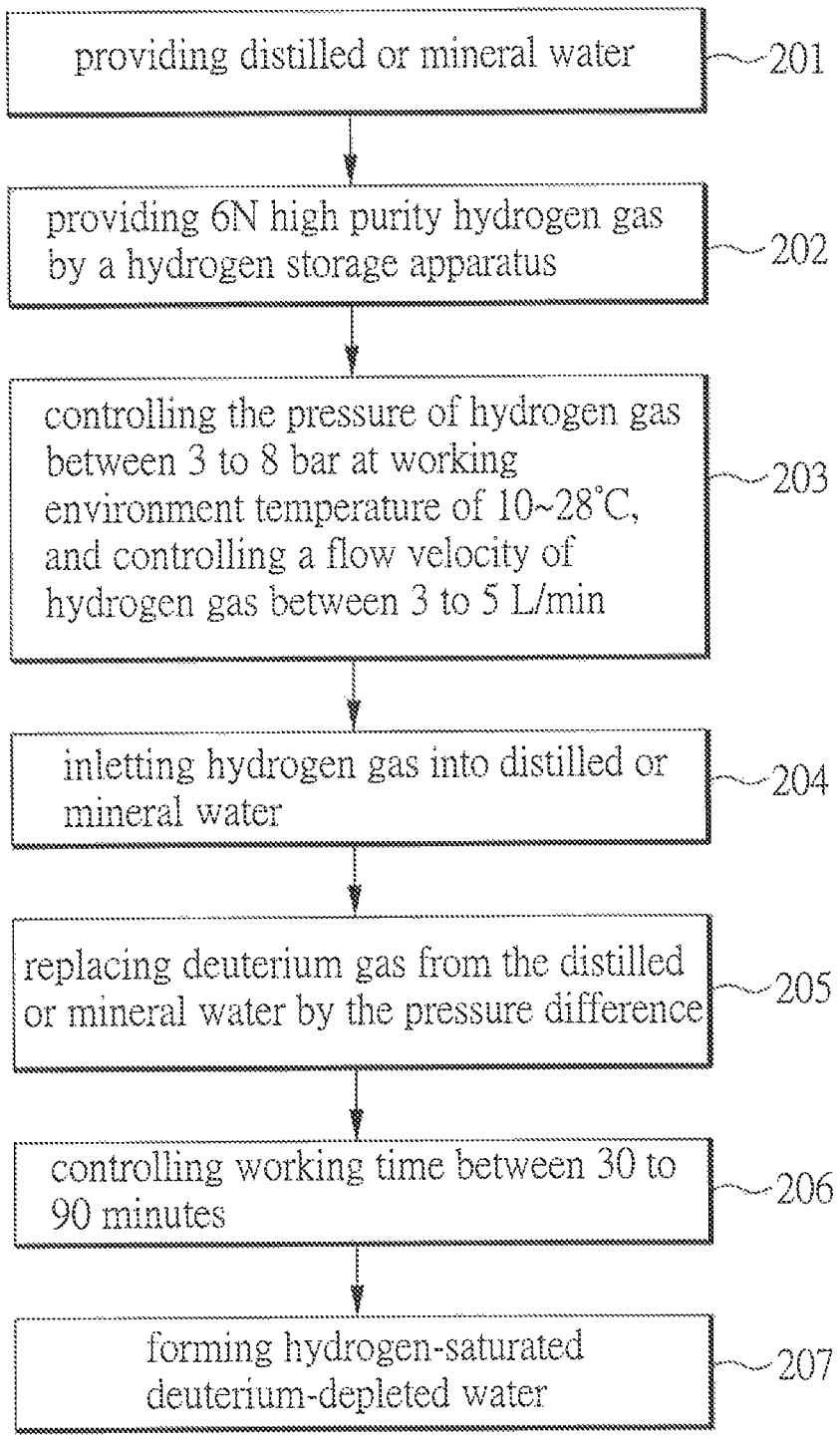
FIG. 2 shows a process flow chart of the hydrogen-saturated deuterium-depleted water according to Example 1 of the present invention.

Please refer to FIG. 2, FIG. 2 shows a process flow chart of the hydrogen-saturated deuterium-depleted water according to Example 1 of the present invention. As shown in FIG. 2, please refer to process 201, a distilled or mineral water is provided and is produced by an electric dialyzator, an ion exchanger, a counter-osmosis device, a distillation equipment and the other appropriate processing method. Please refer to process 202, a high purity hydrogen gas of 6N is provided by a hydrogen storage apparatus. Please refer to process 203, the pressure of the high purity hydrogen gas is controlled between 3 to 8 bars by the pressure regulator valve; and the flow velocity of high purity hydrogen gas is controlled between 3 to 5 L/min by the flow controller; wherein the working environment temperature is controlled by the air conditioner. Please refer to processes 204 and 205, the high purity hydrogen gas is inlet into the distilled water, and the deuterium gas is replaced by the pressure difference. Please refer to process 206, the working time is controlled between 30 to 90 minutes. Please refer to process 207, the produced hydrogen-saturated deuterium-depleted water is sealed for 30 minutes, and sterilized cold filled the hydrogen-saturated deuterium-depleted water to an encapsulating container by a sterilized box at room temperature. Finally, the hydrogen-saturated deuterium-depleted water achieves liquid-vapor equilibration between 15 to 30 days to maintain hydrogen-saturated deuterium-depleted water with high concentration saturated state.

In the method for manufacturing hydrogen-saturated deuterium-depleted water of the present invention, the high purity hydrogen gas is inlet into distilled or mineral water to replace the deuterium gas from the distilled or mineral water by the produced pressure difference; therefore, the hydrogen-saturated deuterium-depleted water having the deuterium content below 130 ppm may be produced, and the hydrogen-saturated deuterium-depleted water with high concentration saturated state may be maintained simultaneously, namely the solubility of hydrogen gas approaches 2%. Besides, in the method for manufacturing hydrogen-saturated deuterium-depleted water of the present invention, the working environment temperature, the pressure of the high purity hydrogen gas, the flow velocity of the high purity hydrogen gas, and the working time may be controlled to achieve optimizing benefit.

It should be understood that these examples are merely illustrative of the present invention and the scope of the invention should not be construed to be defined thereby, and the scope of the present invention will be limited only by the appended claims.

What is claimed is:

1. A method for manufacturing hydrogen-saturated deuterium-depleted water, comprising:
   (a) providing a distilled water or a mineral water;
   (b) providing a hydrogen storage apparatus for providing a high purity hydrogen;
   (c) controlling a pressure of hydrogen between 3~8 bar at a working environment temperature of 10~28° C.;
   (d) controlling a flow velocity of hydrogen between 3~5 L/min and inletting hydrogen into the distilled or mineral water to produce a pressure difference to replace deuterium from the distilled water; and
   (e) controlling a working time between 30~90 minutes to produce a hydrogen-saturated deuterium-depleted water.

2. The method for manufacturing hydrogen-saturated deuterium-depleted water of claim 1, wherein a purity of the high purity hydrogen is in a range of 99.9999% or more.

3. The method for manufacturing hydrogen-saturated deuterium-depleted water of claim 1, wherein a deuterium content of the hydrogen-saturated deuterium-depleted water is 70 ppm to 130 ppm.

4. The method for manufacturing hydrogen-saturated deuterium-depleted water of claim 1, wherein a solubility of hydrogen of the hydrogen-saturated deuterium-depleted water is 1.5 to 2%.

5. The method for manufacturing hydrogen-saturated deuterium-depleted water of claim 1, wherein the hydrogen storage apparatus comprises a pressure regulator valve for controlling a pressure of the hydrogen; and a flow controller for controlling a flow velocity of hydrogen.

6. The method for manufacturing hydrogen-saturated deuterium-depleted water of claim 1, wherein the working environment temperature is controlled by an air conditioner.

7. The method for manufacturing hydrogen-saturated deuterium-depleted water of claim 1, further comprising a step (f): standing and sealing the hydrogen-saturated deuterium-depleted water for 30 to 90 minutes.

8. The method for manufacturing hydrogen-saturated deuterium-depleted water of claim 1, further comprising a step (g): sterilized cold filling the hydrogen-saturated deuterium-depleted water to an encapsulating container by a sterilized box at room temperature.

9. The method for manufacturing hydrogen-saturated deuterium-depleted water of claim 8, wherein the encapsulating container is made by a glass material or a stainless steel material.

10. The method for manufacturing hydrogen-saturated deuterium-depleted water of claim 1, further comprising a step (h): liquid-vapor equilibrating the hydrogen-saturated deuterium-depleted water between 15 to 30 days.

* * * * *